United States Patent [19]

Nist et al.

[11] Patent Number: 5,352,782
[45] Date of Patent: Oct. 4, 1994

[54] PROCESS FOR PREPARING CRYSTALLINE β-LACTAM MONOHYDRATE

[75] Inventors: Robert L. Nist, Greenfield; Marvin E. Wildfeuer, Lafayette, both of Ind.

[73] Assignee: Eli Lilly and Company, Indianapolis, Ind.

[21] Appl. No.: 71,552

[22] Filed: Jun. 4, 1993

[51] Int. Cl.$^5$ .............................................. C07D 487/04
[52] U.S. Cl. ................................... 540/205; 540/215
[58] Field of Search ................. 540/205, 215; 514/210

[56] References Cited

U.S. PATENT DOCUMENTS

| | | | |
|---|---|---|---|
| 3,502,663 | 3/1970 | Barnes, Jr. | 260/243 |
| 3,531,481 | 9/1970 | Pfeiffer | 260/243 |
| 4,977,257 | 12/1990 | Eckrich et al. | 540/205 |

FOREIGN PATENT DOCUMENTS 0311366 5/1988 European Pat. Off. .
0369686 10/1989 European Pat. Off. .

OTHER PUBLICATIONS

U.S. Ser. No. 08/071,550 Jun. 4, 1993 E. F. Plocharczyk, et al.
U.S. Ser. No. 08/077,305 Jun. 15, 1993 Jane G. Amos, et al.
U.S. Ser. No. 08/084,651 Jun. 28, 1993 J. G. Amos, et al.
U.S. Ser. No. 08/072,204 Jun. 4, 1993 W. C. Henning, et al.

*Primary Examiner*—Nicholas Rizzo
*Attorney, Agent, or Firm*—Thomas G. Plant; Gerald V. Dahling; James J. Sales

[57] ABSTRACT

The invention provides a process for the preparation of the crystalline monohydrate form of the compound of the formula (I)

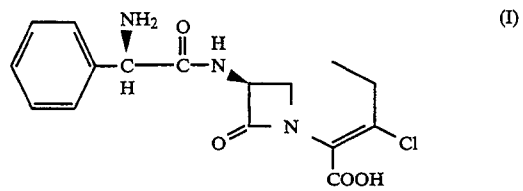

which comprises the step of mixing a form of loracarbef, other than the crystalline monohydrate, such as the ethanol crystal, acetone crystal, crystalline dihydrate, acetonitrile crystal, methanol crystal, propanol crystal, ethyl acetate crystal, methylene chloride crystal, crystalline bis(DMF) and crystalline mono(DMF) form, in water at a temperature between about 30° C. to about 60° C., and preferably at a temperature between 40° C. and 50° C. Conversion may also be accomplished by exposing the loracarbef form to saturated steam at a temperature of between about 90° to about 100° C. Another aspect of the invention is the preparation of the above mentioned crystal forms by slurrying the bis(DMF) solvate form of the compound of formula (I) with the respective solvent.

9 Claims, No Drawings

PROCESS FOR PREPARING CRYSTALLINE β-LACTAM MONOHYDRATE

BACKGROUND OF THE INVENTION

This invention relates to a process for the preparation off a crystalline monohydrate form of a carbacephalosporin.

The β-lactam antibiotic of the formula (I),

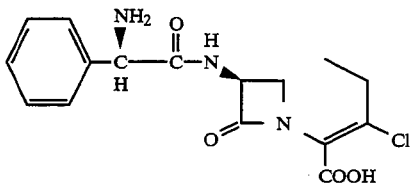

is the potent orally active antibiotic known as loracarbef. The antibiotic is described, for example by J. Hashimoto, et al., in U.S. Pat. No. 4,335,211, issued Jun. 15, 1982.

The above compound comes in various forms, including the crystalline monohydrate form, which is disclosed in European Patent Publication 0,311,366 having a publication date of Apr. 12, 1989. The crystalline dihydrate form of the compound is disclosed in European Patent Publication 369,686 published May 23, 1990. Other known solvate forms of the compound are disclosed in Eckrich et al., U.S. Pat. No. 4,977,257. As set out in the Eckrich et al. patent, the crystalline monohydrate form of loracarbef may be derived from the loracarbef bis(DMF)solvate. The procedure for such conversion involves dissolving the loracarbef bis(DMF-)solvate in water, adding hydrochloric acid followed by triethylamine. The crystalline monohydrate is then filtered from the mixture. This particular process is hampered by the inefficient removal of residual dimethylformamide (present in the intermediate loracarbef bis(DMF)solvate), and triethylamine (used to crystallize loracarbef monohydrate) from the crystals slow filtration and wash difficulties.

It has been determined that loracarbef crystalline monohydrate, which is a fine "hair-like" crystal, apparently forms a mat on the filter medium which prevents or reduces the ability to remove the occluded solvent and base. In order to obtain acceptable levels of the DMF and triethylamine it has been necessary to wash the crystals with water one or more times. Since loracarbef monohydrate is moderately soluble in water (approximately 10 mg/ml) significant yield losses result when such reslurries are needed. Added to this is the slow filterability in General of the monohydrate.

In light of the above difficulties, what is needed is a process which avoids not only the need to use acids and bases to produce the monohydrate, but also avoids the requirement for filtration, requiring only a dry down to produce the monohydrate.

SUMMARY OF THE INVENTION

The invention provides a process for the preparation of the crystalline monohydrate form of the compound of the formula (I)

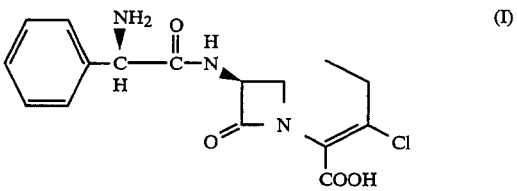

which comprises the step of mixing a form of loracarbef other than the crystalline monohydrate, such as the ethanol crystal, acetone crystal, crystalline dihydrate, acetonitrile crystal, methanol crystal, propanol crystal, ethyl acetate crystal, methylene chloride crystal, and crystalline his or mono(DMF) form of the compound of formula (I), in water at a temperature between about 30° C. to about 60° C., and preferably at a temperature between 40° C. and 50° C. Conversion may also be accomplished by exposing the loracarbef form to saturated steam at a temperature of between about 90° to about 100° C. Another aspect of the invention is the preparation of the above mentioned crystal forms by slurrying the bis(DMF)solvate form of the compound of formula (I) with the respective solvent.

DESCRIPTION OF THE INVENTION

In order to find a process for preparing crystalline monohydrate with the desired characteristics, loracarbef dihydrate was slurried in water and heated to 50° C., without the addition of acid or base. Within minutes the dihydrate plates which were initially present converted to small hair-like crystals characteristic of the monohydrate. X-ray data later confirmed that indeed the monohydrate had been obtained by this route.

To see how general this conversion would be, Loracarbef bis(DMF)solvate crystals were slurried in water at 50° C. and these also converted to the monohydrate. However, the problem of residual DMF existed, as DMF has a relatively high boiling point (153° C.)

This problem was circumvented by reslurrying loracarbef disolvate in ethanol, which has a much lower boiling point (78.5° C.) which effectively displaces the dimethylformamide from the crystal, and forms an ethanol crystal form of loracarbef. This proved to be the key to converting the bis(DMF)solvate to the monohydrate in good yield and with acceptable quality. It was determined that acetone as well is able to displace the dimethylformamide. Experiments have shown this route was capable of giving good yields and acceptable product. Other organic solvents, such as methanol, isopropanol, propanol, ethyl acetate, methylene chloride and acetonitrile may also be used in the solvent exchange. Important characteristics for the solvent are that they be relatively volatile (Bp<100C) and are miscible in the system.

The crystal solvent forms of loracarbef are formed by slurrying the crystalline bis(DMF)solvate of the compound of formula (I) with the solvent, and without need of addition of acid or base. The amount of the solvent used should be about 50 ml to 100 ml per 7 g of the DMF disolvate. It has been determined that ethanol and acetone can remove DMF with virtually no yield loss.

It should be understood, however, that the reslurry or steam conversion applies to intermediate forms containing solvents such as dimethylformamide (DMF), the advantage being the avoidance of using acids or bases to result in the crystalline monohydrate. Therefore, all forms of loracarbef may be used in these processes, the use of those forms with a low boiling point solvent being preferred.

The loracarbef forms, when slurried in water at a temperature between about 30° C. to about 60° C., and preferably at a temperature between 40° C. to 50° C., convert to an acceptable loracarbef monohydrate crystal without the heed for addition of acid or base. Also, a conversion may be accomplished by purging saturated steam at a temperature of between about 90° C. to 100° C. through the loracarbef form.

Since the dihydrate can be more efficiently water washed than the monohydrate, a dihydrate intermediate can be crystallized to facilitate the removal of dimethylformamide and triethylamine (or other base) followed by the reslurry conversion to the monohydrate.

Experiments using 50° C. reslurry conversions are summarized in Table 1. In these experiments, a dihydrate, an ethanol crystal derived from DMF disolvate, and an acetone crystal derived from DMF disolvate, were converted to the monohydrate crystal. The residual DMF in the monohydrate slightly exceeded the desired limit, although subsequent experiments were able to achieve levels well below that limit.

TABLE 1

| | Yield % | Anhydrous Potency % | Related Subs % | DMF % | $H_2O$ KF % |
|---|---|---|---|---|---|
| Dihydrate | 79.2 | 98.8 | 0.11 | 0.22 | 4.6 |
| Ethanol Crystal | 85.0 | 98.5 | 0.16 | 0.41 | 4.3 |
| Acetone Crystal | 81.3 | 98.7 | 0.16 | 0.22 | 4.6 |
| Specifications | | 95–105 | <2 | <0.1 | 3.5–6.0 |

As the water reslurry step is primarily used to convert one crystal form to another and is not necessarily a purification step, this opens up several additional process advantages. The mother liquors may be recycled back to the reslurry process to be used instead of water alone, as the mother liquors would not contain acid or base as with the prior processes. This would eliminate the need for a second crop crystallization and also reduce yield losses since second crop yields are only about 80%. Therefore, when the term "water" is used, this includes water which may have other solvents or contaminants therein.

To take this a step further, another approach could be to dry down the final slurry and obtain an acceptable loracarbef monohydrate product. This would avoid the filtration of the crystalline monohydrate, also avoiding milling steps and second crops since, of course, no filtrate would be generated. Yields by this route should be almost quantitative. In the prior processes, acid and/or base is used to precipitate the monohydrate. As no acid or base is needed in this water reslurry process, drying of the resulting monohydrate mixture, without need for precipitation and filtration, will result in an acceptable monohydrate.

Additionally, there is potential for the water reslurry conversion to be used in the pharmaceutical area for preparing a "ready to use" pediatric formulation. This is because loracarbef monohydrate, after drying and milling, no longer resembles the fine hair-like crystals prior to such manipulations. As such, the slurry characteristics are not as desirable, as compared to the original crystal monohydrate slurry which has a "milkshake" consistency and separates slowly. By using a precursor to the crystalline monodydrate, carrying out the water reslurry as part of the pediatric formulation process, it should be possible to retain the desired slurry characteristics.

EXPERIMENTAL SECTION

Example 1

Crystalline Monohydrate

Loracarbef dihydrate 10.0 g (7.7 bg) was slurried in 70 ml $H_2O$ and the temperature was raised to 50° C. After ~10 minutes conversion appeared to be complete. The slurry was cooled to 25° and was harvested on a 7 cm Buchner funnel with Whatman filter 1. Filtration was slow. Mother liquor was used to rinse flask; ~5 ml $H_2O$ wash was applied. The crystals were dried overnight in the vacuum oven at 45° C. Wgt: 7.29 g, Purity: 94.3% (98.8% anhydrous), DMF: 0.22%, KF: 4.6%, Rel. Subs: 0.11%, K+: 0.5%, Cl−: 0.5%, Yield: 89.2% X-ray analysis: monohydrate.

Example 2

Loracarbef Ethanol Crystal

Loracarbef bis(DMF)solvate(7.0 g, 5.0 bg) was slurried in 50 ml 3A EtOH for 15 minutes (no noticeable change under microscope). The crystals were filtered on a 5.5 cm Buchner funnel with a Whatman 1 filter (fast filtration). The crystals were washed with ~7 ml EtOH. The crystals were dried in the vacuum oven for two hours at 45° C. Wgt: 5.41 g, Purity: 94.5%, DMF: 2.73%, KF: 0.3%, Rel. Subs: 0.16%, Yield: 101.4%

Example 3

Ethanol Crystal to Loracarbef Monohydrate

Loracarbef ethanol crystal (3.5 g, 3.3 bg) was slurried in 25 ml $H_2O$ and heated to 50° C. The slurry became thick and was diluted to about 40 ml with water. After ~30 minutes, monohydrate crystals appeared. The slurry was harvested on a 4.25 cm Buchner funnel with a Whatman 1 filter. Mother liquor was used to rinse flask, but no wash was applied. The crystals were dried in the vacuum oven ~7 hrs at 45° C. Wgt: 2.94 g, Purity: 94.3% (98.5% anhydrous), DMF: 0.41%, KF: 4.3%, Rel. Subs: 0.16%, Yield: 83.8%. X-ray analysis: Monohydrate.

Example 4

Loracarbef Acetone Crystal

Loracarbef DMF disolvate 7.0 g (50 bg) was slurried in 50 ml acetone for 15 minutes (no noticeable change under microscope). The crystals were filtered on a 5.5 cm Buchner funnel with a Whatman 1 filter (fast filtration). The crystals were washed with ~7 ml acetone. The crystals were dried in the vacuum oven for two hours at 45° C. Wgt: 5.66 g, Purity: 90.4%, DMF: 3.15%, KF: 4.3%, Rel. Subs: 0.23%, Yield: 101.5%

Example 5

Acetone Crystal to Loracarbef Monohydrate

Loracarbef acetone crystal (3.5 g, 3.2 bg) was slurried in 40 ml $H_2O$ and heated to 50° C. After ~30 minutes crystals appeared. The slurry was harvested on a 4.25 cm Buchner funnel with a Whatman 1 filter. Mother liquor was used to rinse flask, but no wash was applied. The crystals were dried in the vacuum oven ~7 hrs at 45° C. Wgt: 2.69 g, Purity: 94.2% (98.7% anhydrous), DMF: 0.22%, KF: 4.6%, Rel. Subs: 0.16%, Yield: 80.1% X-ray analysis: Monohydrate Example 6

Recycle of Monohydrate Mother Liquor for Reslurry of Ethanol Crystal

I. Loracarbef ethanol crystal (2.0 g 1 95 bg) was reslurried in 35 ml H₂O and heated to 50° C. After ~20 minutes the material converted to monohydrate. The slurry was harvested on a 4.25 cm Buchner funnel with a Whatman 1 filter. The cake was washed with ~5 ml H₂O. The crystals were dried in the vacuum oven overnight at 45° C. Wgt: 1.61 g, Purity: 94.6% (98.9% anhydrous), DMF: 0.00%, KF: 4.3%, Related Subs: 0.14%, Yield: 80.0%

II. Loracarbef ethanol crystal (2.0 g 1.95 bg) was reslurried in the mother liquor from I and heated to 50° C. After ~20 minutes crystals converted to monohydrate. The slurry was harvested on a 4.25 cm Buchner funnel with a Whatman 1 filter. The cake was washed with ~5 ml H₂O. The crystals were dried in the vacuum oven overnight at 45° C. Wgt: 1.98 g, Purity: 94.5% (98.4% anhydrous), DMF: 0.01%, KF: 4.0%, Related Subs: 0.16%, Yield: 97.6%

III. Loracarbef ethanol crystal (2.0 g, 1.95 bg) was reslurried in the mother liquor from II and heated to 50° C. After ~20 minutes crystals converted to monohydrate. The slurry was harvested on a 4.25 cm Buchner funnel with Whatman 1. The cake was washed with ~7 ml H₂O. The crystals were dried in the vacuum oven overnight at 45° C. Wgt: 1.94 g, Purity: 93.9% (98.0% anhydrous), DMF: 0.01%, KF: 4.2%, Related Subs: 0.15%, Yield: 95.1%

IV. Loracarbef ethanol crystal (2.0 g, 1.95 bg) was reslurried in the mother liquor from III and heated to 50° C. After ~20 minutes crystals converted to monohydrate. The slurry was harvested on a 4.25 cm Buchner funnel with Whatman 1. The cake was washed with ~10 ml H₂O. The crystals were dried in the vacuum oven overnight at 45° C. Wgt: 2.08 g, Purity: 93.9% (97.9% anhydrous), DMF: 0.02%, KF: 4.1%, Related Subs: 0.18%, Yield: 101.8%

V. Loracarbef ethanol crystal (2.0 g, 1.95 bg) was reslurried in the mother liquor from IV and heated to 50° C. After ~20 minutes crystals converted to monohydrate. The slurry was harvested on a 4.25 cm Buchner funnel with Whatman 1. The cake was washed with ~5 ml H₂O. The crystals were dried in the vacuum oven overnight at 45° C. Wgt: 1.94 g, Purity: 93.5% (97.7% anhydrous), DMF: 0.02%, KF: 4.3%, Related Subs: 0.13%, Yield: 94.6%

I claim:

1. A process for the preparation of the crystalline monohydrate form of the compound of the formula (I):

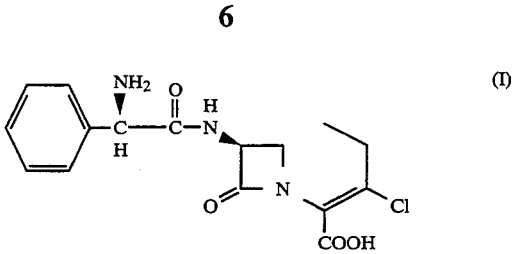

which comprises the step of
   (a) mixing a form of the compound of formula (I), other than the crystalline monohydrate form, in water at a temperature between about 30° to about 60° C.; or
   (b) exposing a form of the compound of formula (I), other than the crystalline monohydrate form, to saturated steam at a temperature of between about 90° C. to about 100° C.

2. The process as recited in claim 1 wherein the water temperature is between 40° C. and 50° C.

3. The process as recited in claim 1 wherein the form of loracarbef is selected from the ethanol crystal, acetone crystal, crystalline dihydrate, acetonitrile crystal, methanol crystal, propanol crystal, ethyl acelate crystal, methylene chloride crystal, crystalline bis(DMF) or crystalline mono(DMF) form.

4. The process as recited in claim 3 wherein said form is ethanol crystal, acetone crystal, acetonitrile crystal, methanol crystal, propanol crystal, ethyl acetate crystal or methylene chloride crystal form.

5. The process as recited in claim 4 further comprising the step of forming the solvent crystal form of the compound by slurrying the crystalline bis(DMF) solvate form of the compound with the respective solvent.

6. The process as recited in claim 5 wherein said solvent is ethanol or acetone.

7. The process as recited in claim 1 further comprising the step of drying the crystalline monohydrate.

8. The process as recited in claim 1 further comprising the step of filtering the crystalline monohydrate.

9. A process for the preparation of the crystalline monohydrate form of the compound of the formula (I):

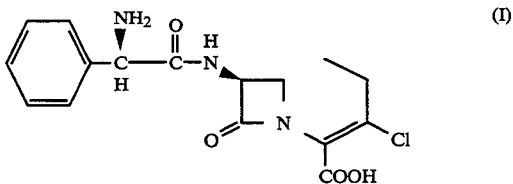

which comprises the step of mixing a form of the compound of formula (I), other than the crystalline monohydrate form, in water at a temperature between about 30° to about 60° C.

* * * * *

UNITED STATES PATENT AND TRADEMARK OFFICE
CERTIFICATE OF CORRECTION

PATENT NO. : 5,352,782

DATED : October 4, 1994

INVENTOR(S) : Nist, Robert L. et al

It is certified that error appears in the above-indentified patent and that said Letters Patent is hereby corrected as shown below:

The structure of the compound of formula (I) is wrong throughout the patent. The structure appears throughout the patent as:

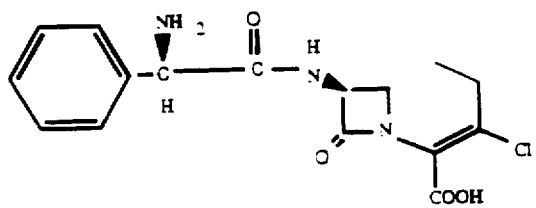

The structure should appear in the abstract, in columns 1, 2 and 3, and in (Claim 1 & 9) as follows:

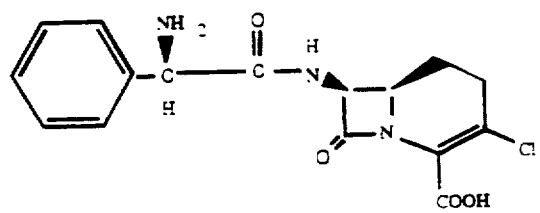

UNITED STATES PATENT AND TRADEMARK OFFICE
CERTIFICATE OF CORRECTION

PATENT NO. : 5,352,782
DATED : October 4, 1994
INVENTOR(S) : Nist, Robert L. et al It is certified that error appears in the above-indentified patent and that said Letters Patent is hereby corrected as shown below:

Column 1, line 3, "off a" should read -- of a --.

Column 1, line 37-38, "bis(DMF-)solvate" should read -- bis (DMF)-solvate --.

Column 2, line 36, "Lora-" should read -- lora- --.

Column 3, line 8, "heed" should read -- need --.

Column 4, line 50, "(50 bg)" should read -- (5.0 bg) --.

Column 5, line 3, "(2.0 g 195)" should read -- (2.0 g, 1.95 bg) --.

Signed and Sealed this

Fourteenth Day of November, 1995

BRUCE LEHMAN

*Attest:*

*Attesting Officer*  *Commissioner of Patents and Trademarks*